United States Patent [19]

Owen et al.

[11] Patent Number: 4,675,461

[45] **Date of Patent: * Jun. 23, 1987**

[54] CONVERSION OF LPG HYDROCARBONS INTO DISTILLATE FUELS USING AN INTEGRAL LPG DEHYDROGENATION-MOGD PROCESS

[75] Inventors: Hartley Owen, Belle Mead; John C. Zahner, Princeton, both of N.J.

[73] Assignee: Mobil Oil Corporation, New York, N.Y.

[ * ] Notice: The portion of the term of this patent subsequent to May 22, 2001 has been disclaimed.

[21] Appl. No.: 837,864

[22] Filed: Mar. 5, 1986

Related U.S. Application Data

[63] Continuation of Ser. No. 650,597, Sep. 14, 1984, abandoned, and a continuation-in-part of Ser. No. 593,462, Mar. 27, 1985, which is a continuation-in-part of Ser. No. 508,907, Jun. 29, 1983, Pat. No. 4,450,311.

[51] Int. Cl.[4] .......................... C07C 2/00; C07C 2/12

[52] U.S. Cl. .................................. 585/330; 585/319; 585/315; 585/415; 585/413

[58] Field of Search ............... 585/330, 319, 415, 413, 585/654, 300, 301, 441, 719, 315

[56] References Cited

U.S. PATENT DOCUMENTS

| | | | |
|---|---|---|---|
| 2,270,086 | 1/1942 | Seguy | 196/10 |
| 2,764,622 | 9/1956 | Marisic et al. | 585/654 |
| 3,607,734 | 9/1971 | Stafford | 208/341 |
| 3,714,024 | 1/1973 | Youngblood et al. | 208/78 |
| 3,799,864 | 3/1974 | Bunn et al. | 208/80 |
| 3,928,174 | 12/1975 | Bonacci et al. | 585/300 |
| 3,960,978 | 6/1976 | Givens et al. | 260/683 |
| 4,012,455 | 3/1977 | Owen et al. | 260/668 R |
| 4,021,502 | 5/1977 | Plank et al. | 260/683 |
| 4,032,432 | 6/1977 | Owen | 208/70 |
| 4,100,218 | 7/1978 | Chen et al. | 260/673 |
| 4,150,062 | 4/1979 | Garwood et al. | 260/673 |
| 4,191,846 | 3/1980 | Farha, Jr. et al. | 585/440 |
| 4,197,185 | 4/1980 | LePage et al. | 208/71 |
| 4,211,640 | 7/1980 | Garwood et al. | 208/255 |
| 4,216,346 | 8/1980 | Antos | 585/660 |
| 4,227,992 | 10/1980 | Garwood et al. | 208/46 |
| 4,376,225 | 3/1983 | Vora | 585/660 |
| 4,413,153 | 11/1983 | Garwood et al. | 585/304 |
| 4,433,185 | 2/1984 | Tabak | 585/312 |
| 4,450,311 | 5/1984 | Wright et al. | 585/315 |
| 4,456,781 | 6/1984 | Marsh et al. | 585/533 |
| 4,497,968 | 2/1985 | Wright et al. | 585/304 |

OTHER PUBLICATIONS

Kirk-Othmer, *Encyclopedia of Chemical Technology*, 3d Ed, vol. 19, "Powder Coatings to Recycling", pp. 232-235 (Propylene); John Wiley & Sons, 1979.

*Oil & Gas Journal*—Dec. 8, 1980, "Dehydrogenation Links LPG to More Octanes", pp. 96-101; S. Gussow et al., Houdry Div., Air Products & Chemicals, Inc., Allentown, Pa.

*Hydorcarbon Processing*, Apr. 1982, "$C_2/C_5$ Dehydrogenation Updated" by B. V. Vora and T. Imai, UOP Inc., Des Plaines, Ill., pp. 171-174.

*Primary Examiner*—Andrew H. Metz

*Assistant Examiner*—Chung K. Pak

*Attorney, Agent, or Firm*—Alexander J. McKillop; Michael G. Gilman; L. G. Wise

[57] ABSTRACT

Disclosed is a method and apparatus for conversion of LPG hydrocarbons into distillate fuels by integrating LPG dehydrogenation with catalytic oligomerization and recovering the distillates produced. The described method and apparatus may comprise an $H_2$ separation zone, wherein a lean oil stream contacts a dehydrogenation effluent stream to produce a $C_3+$ rich liquid stream to feed oligomerization. An energy efficient separation zone comprising dual debutanizers is disclosed. In addition, a method and apparatus is disclosed for a fluid bed dehydrogenation reactor zone using an FCC catalyst contaminated with a metal, such as nickel and/or vanadium.

1 Claim, 4 Drawing Figures

CONVERSION OF LPG HYDROCARBONS INTO DISTILLATE FUELS USING AN INTEGRAL LPG DEHYDROGENATION-MOGD PROCESS

REFERENCE TO RELATED APPLICATION

This application is a continuation of U.S. patent application Ser. No. 650,597 filed Sept. 14, 1984 (now abandoned); and a continuation-in-part of copending application Ser. No. 593,462, filed Mar. 27, 1985, which is a continuation-in-part of application Ser. No. 508,907, filed June 29, 1983, now U.S. Pat. No. 4,450,311.

BACKGROUND OF THE INVENTION

1. Field of the Invention

This invention relates to a method and apparatus for converting LPG boiling range paraffins to heavier hydrocarbons, such as gasoline range or distillate range fuels. In particular, it relates to methods and apparatus for doing so, which integrate the operation of catalytic or thermal dehydrogenation of a paraffinic feedstock to produce olefins with the operation of a catalytic reactor zone to convert olefins to heavier hydrocarbons, and which further include downstream separation of heavier hydrocarbons to optimize product selectivity and minimize the heat requirement. The method and apparatus may also include a fluid bed dehydrogenation zone to dehydrogenate paraffins to olefins.

2. Discussion of the Prior Art

The conversion of light paraffins, such as propane and butane, to mono-olefins, such as propylene and butylene, has been accomplished by thermal or catalytic dehydrogenation. A general discussion of thermal dehydrogenation (i.e., steam cracking) is presented in *Encyclopedia of Chemical Technology,* Ed. by Kirk and Othmer, Vol. 19, 1982, Third Ed., pp. 232–235. Various processes for catalytic dehydrogenation are available in the prior art. These processes include the Houdry Catofin process by Air Products and Chemicals Inc., Allentown, PA, the Oleflex process by UOP, Des Plaines, IL, and a process disclosed by U.S. Pat. No. 4,191,846. The Houdry Catofin process, described in a magazine article, "Dehydrogenation Links LPG to More Octanes", Gussow et al, *Oil and Gas Journal,* Dec. 8, 1980, involves a fixed bed, multi-reactor catalytic process for conversion of paraffins to olefins. Typically, the Houdry Catofin process runs at low pressures of 5–30 inches of mercury absolute, and high temperatures with hot reactor effluent at 550°–650° C. Dehydrogenation is an endothermic reaction, so it normally requires a furnace to heat a feedstream prior to feeding the feedstream into the reactors. The Oleflex process disclosed in an article "$C_2/C_5$ Dehydrogenation Updated", Verrow et al, *Hydrocarbon Processing,* April 1982, uses stacked catalytic reactors with hydrogen recycle. U.S. Pat. No. 4,191,846 teaches the use of Group VIII metal containing catalysts to promote catalytic dehydrogenation of paraffins to olefins.

Recent developments in zeolite catalysts and hydrocarbon conversion methods and apparatus have created interest in utilizing olefinic feedstocks for producing heavier hydrocarbons, such as $C_5+$ gasoline or distillate. These developments have contributed to the development of the Mobil olefins to gasoline/distillate (MOGD) method and apparatus.

In MOGD, olefins are catalytically converted to heavier hydrocarbons by catalytic oligomerization using an acid crystalline zeolite, such as a ZSM-5 type catalyst. Process conditions can be varied to favor the formation of either gasoline or distillate range products. In U.S. Pat. Nos. 3,960,978 and 4,021,502, Plank, Rosinski and Givens disclose conversion of $C_2$–$C_5$ olefins, alone or in combination with paraffinic components, into heavier hydrocarbons over a crystalline zeolite catalyst. Garwood et al have contributed improved processing techniques to the MOGD system, as disclosed in U.S. Pat. Nos. 4,150,062; 4,211,640; and 4,227,992. Marsh et al, as disclosed in U.S. Pat. No 4,456,781, provided improved processing techniques for the MOGD system. U.S. Pat. No. 3,760,024 to Cattanach discloses contacting olefins with ZSM-5 type zeolite catalyst to form aromatics.

The conversion of olefins in a MOGD system may occur in a gasoline mode or a distillate mode. In the gasoline mode, the olefins are catalytically oligomerized at temperature ranging from 400°–800° F. and pressure ranging from 10–1000 psia. To avoid excessive temperatures in the exothermic reactor, the olefinic feed may be diluted. In the gasoline mode, the diluent may comprise light hydrocarbons, such as $C_3$–$C_4$, from the feedstock and/or recycled from debutanized product. In the distillate mode, olefins are catalytically oligomerized at temperature ranging from 300°–600° F. and pressure ranging from 400–1000 psig. In the distillate mode operation, olefinic gasoline may be recycled and further oligomerized, as disclosed in U.S. Pat. No. 4,211,640 (Garwood et al).

Olefinic feedstocks may be obtained from various sources, including from fossil fuel processing streams, such as gas separation units, from cracking of $C_2^{30}$ hydrocarbons, from coal by-products and from various synthetic fuels processing streams. U.S. Pat. No. 4,100,218 (Chen et al) teaches thermal cracking of ethane to ethylene, with subsequent conversion of ethylene to LPG and gasoline over a ZSM-5 type zeolite catalyst.

Although gasoline and distillate can be produced from propane and butane by the prior art using dehydrogenation integrated with MOGD, there are several problems with integrating these processes. For example, U.S. Pat. No. 4,413,153 (Garwood et al) discloses a system which catalytically (or thermally) dehydrogenates the paraffins to olefins, and then reacts the olefins by catalytic oligomerization (MOGD) to distillate range material. Catalytic oligomerization in the distillate mode is a high (preferably greater than 600 psig) pressure process, whereas dehydrogenation is favored by lower (less than 25 psig) pressure.

Typically, $H_2$ separation of the dehydrogenation effluent stream could be accomplished by feeding the stream to an absorber. In the absorber, the dehydrogenation effluent stream contacts with a lean oil stream, which absorbs $C_3+$ material from the dehydrogenation effluent stream to form a $C_3+$ rich stream. Meanwhile, $H_2$ and light gases exit the absorber in a $C_2-$ rich stream. The $C_3+$ rich stream is sent to a debutanizer to form a debutanizer overhead stream and a debutanizer bottoms stream.

The debutanizer bottoms stream forms the lean oil stream which is recycled to the absorber. Thus, the absorber has a lean oil stream circuit which is independent of downstream processing. Typically, the debutanizer overhead stream comprising $C_3$'s and $C_4$'s would pass to an oligomerization reactor zone, where, in order to increase the distillate yield from the oligomerization reactor zone, it is combined with a recycle gasoline stream comprising $C_5+$ olefins recovered from an oligomerization reactor zone effluent.

It is difficult to efficiently separate the effluents from the oligomerization reactor zone to provide a recycle gasoline stream to the oligomerization reactor zone as well as a gasoline product stream. One such separation system, disclosed in U.S. Pat. No. 4,456,781 to Marsh et al, separates oligomerization reactor effluent in a debutanizer to form a $C_5+$ bottoms stream, which is fed to a splitter where it vaporizes all the gasoline to form a gasoline product overhead stream and a distillate product bottoms stream. It is inefficient because the gasoline is vaporized only to be subsequently cooled to a liquid. It would be more efficient to recover gasoline for recycle as a liquid prior to the splitter to conserve the energy required to vaporize the gasoline recycle.

Another problem with integration of dehydrogenation with oligomerization is the dehydrogenation of LPG paraffins to olefins is thermodynamically unfavored and very endothermic. Supplying heat for the process leads to a significant part of the process costs for current technology. U.S. Pat. No. 4,032,432 combines the operation of a fluid catalytic cracking (FCC) unit with a catalytic oligomerization zone to send heat from the FCC unit to the catalytic oligomerization zone. However, catalytic dehydrogenation of LPG range paraffins has not been combined with an FCC unit to recover heat.

SUMMARY OF THE INVENTION

The invention extensively integrates an LPG dehydrogenation process with an MOGD process to efficiently convert LPG to gasoline and distillate. Central to the invention is the arrangement and interrelationship of five process elements: main absorber, oligomerization (MOGD) reaction zone, separator at high temperature and low pressure; and two debutanizers.

The invention facilitates separation of $H_2$ and light gases ($C_2-$) from a dehydrogenation effluent stream, while using the main absorber, by feeding an entire $C_3+$ rich stream from the main absorber to the oligomerization reactor zone. This eliminates the debutanizer of the above-mentioned prior art, which separated the $C_3+$ rich stream into a debutanizer overhead stream for feeding to the oligomerization reactor zone, and a debutanizer bottoms stream which formed a lean oil stream, comprising $C_5+$ hydrocarbons. In addition, a portion of the $C_5+$ hydrocarbons in the lean oil stream, and subsequently the $C_3+$ rich stream, are $C_5+$ olefins. Therefore, the invention facilitates recycle of $C_5+$ olefins to the oligomerization reactor zone, where they oligomerize to form heavier hydrocarbons.

The invention also provides a heavier hydrocarbon separation zone, which is an energy efficient method and apparatus for separating effluent from the catalytic oligomerization reactor zone by using a high temperature separator and dual debutanizers. The high temperature separator operates at low pressure, namely, a pressure lower than that of the catalytic oligomerization reactor zone. At start of cycle there is preferably no cooling of the oligomerization zone effluent prior to the separator, although there may be cooling due to the phase change in the separator. The dual debutanizers comprise a recycle debutanizer to recover $C_5+$ material for a lean oil stream, which is recycled to oligomerizaion, and a product debutanizer to recovery material which is subsequently separated into gasoline and distillate product streams.

The invention provides a method and apparatus for supplying heat to a zone for catalytic dehydrogenation of paraffins by employing a transport-type reaction system, similar to the Fluid Catalytic Cracking (FCC) process, which employs fluidizable-type catalysts. The heat could also be supplied to a zone for catalytic dehydrogenation of paraffins by conducting dehydrogenation reactions in one or more risers of a multi-riser FCC system.

Accordingly, it is a primary object of this invention to provide a method and appartus for converting paraffins to gasoline/distillate by dehydrogenation of LPG to form olefins, contacting a dehydrogenation effluent stream, comprising the olefins, with a lean oil stream, comprising $C_5+$, which absorbs $C_3+$ from the effluent stream to form a $C_3+$ rich stream, feeding the $C_3+$ rich stream to an oligomerization zone, converting the olefins to gasoline-distillate in a catalytic oligomerization reactor zone and separating the gasoline/distillate into desired streams by a separation system employing dual debutanizers.

Another object of this invention is to provide a method and apparatus in which a lean oil stream comprises $C_5+$ olefins and absorbs $C_3+$ from a dehydrogenation effluent stream and portions of both the $C_5+$ and $C_3+$ olefins oligomerize in the oligomerization reactor zone.

Another object of this invention is to provide a method and apparatus in which a lean oil stream absorbs $C_3+$ from a dehydrogenation zone effluent stream and the unabsorbed $C_2^-$ passes to a sponge absorber to recover a $H_2$ rich gas.

Another object of this invention is to provide a method and apparatus for feeding $C_4^-$ olefins in a liquid stream to a catalytic oligomerization reactor zone.

Another object of this invention is to provide an energy-saving method and apparatus comprising dual debutanizers for efficiently separating hydrocarbons from a catalytic oligomerization reactor zone into a lean oil stream, for recycle to a catalytic oligomerization reactor zone, and a variety of products.

Another object of this invention is to provide a method and apparatus of providing heat to a catalytic dehydrogenation of paraffins zone in a transport-type reactor zone which employs fluidizable-type catalysts.

Another object of this invention is to provide a method and apparatus for providing heat to a catalytic dehydrogenation of paraffins zone by taking heat from a unit for fluid catalytic cracking (FCC) of hydrocarbons.

In its apparatus respects, the invention comprises a means for feeding an LPG feedstream to a dehydrogenation zone comprising means for dehydrogenating, cooling and compressing the LPG to produce a dehydrogenation effluent stream; an $H_2$ separation zone for separating $C_2^-$ and $H_2$ from the dehydrogenation effluent stream of contacting said effluent with a lean oil stream, comprising $C_5+$ hydrocarbons, which absorbs $C_3+$ from said effluent stream to form a $C_3+$ rich liquid stream; passing the $C_3+$ rich stream into an oligomerization reactor zone (MOGD) for contacting olefins with an oligomerization catalyst and converting a portion, typically 85–98%, of the $C_3$–$C_4$ olefins to gasoline and distillate boiling range materials which form a reactor effluent stream. The oligomerization reactor zone contains a crystalline zeolite catalyst, preferably maintained at a pressure of about 400–1000 psig, a temperature of about 300°–600° F., and a space velocity of about 0.1–10 weight hourly space velocity (WHSV) with regard to $C_3$ and heavier olefins. In addition, the lean oil stream preferably comprises $C_5+$ olefins which oligomerize to form heavier hydrocarbons in the catalytic oligomerization reactor zone.

The apparatus may further comprise a heavier hydrocarbon separation zone comprising a high temperature separator, which operates at a lower pressure than the oligomerization zone, and dual debutanizers to separate the reactor effluent stream into a gasoline product stream, a distillate product stream, an unconverted LPG stream for recycle to the dehydrogentation zone and the lean oil stream for recycle to the oligomerization reactor zone.

In its method respects the invention comprises the steps of feeding an LPG feedstream to a dehydrogenation zone; dehydrogenating, cooling, and compressing the LPG within the dehydrogenation zone to produce a dehydrogenation effluent stream; separating $C_2-$ and $H_2$ from the dehydrogenation effluent stream in an $H_2$ separation zone to form a liquid $C_3+$ rich stream; passing the $C_3+$ rich stream into an oligomerization reactor zone; and contacting the $C_3+$ rich stream with oligomerization catalyst in the oligomerization reactor zone to convert typically 85–98% of the $C_3$–$C_4$ olefins to gasoline and distillate boiling range materials which form a reactor effluent stream. The oligomerization reactor zone contains a crystalline zeolite catalyst, preferably maintained at a pressure of about 400–1000 psig, a temperature of about 300°–600° F., and a space velocity of about 0.1–10 WHSV with regard to $C_3$ and higher olefins. In addition, the lean oil stream comprises $C_5+$ olefins which oligomerize to form heavier hydrocarbons in the catalytic oligomerization reactor zone.

The method may further comprise the steps of passing the reactor effluent stream to a heavier hydrocarbon separation zone, comprising a high temperature separator, which operates at a lower pressure than the oligomerization zone, and dual debutanizers, to form a gasoline product stream, a distillate product stream, an unconverted LPG stream for recycle to the dehydrogenation zone, and the lean oil stream for recycle to the oligomerization reactor.

Rather than use a conventional catalytic dehydrogenation zone, the catalytic dehydrogenation zone may comprise a catalytic reactor, a catalytic regenerator, and a dehydrogenation riser much like a Fluid Catalytic Cracking (FCC) unit. An LPG feedstream is dehydrogenated by being combined with a crystalline zeolite catalyst, and being passed through the dehydrogenation riser from the catalytic regenerator to the catalytic reactor. In another embodiment, the dehydrogenation zone could comprise a fluid catalytic cracking (FCC) unit with multiple risers so that paraffin dehydrogenation could occur in a first riser, while fluid catalytic cracking of hydrocarbons could occur in a second riser. In another embodiment, dehydrogenation of LPG and catalytic cracking of hydrocarbons may occur in the same riser.

In an alternate embodiment of the method and apparatus for converting paraffins to gasoline/distillate, hydrogen is removed from a dehydrogenated paraffins stream within the dehydrogenation zone, in which case the $H_2$ separation zone can be omitted.

DETAILED DESCRIPTION OF THE INVENTION

By way of background, the dehydrogenation of light paraffins (e.g., LPG) to olefins can be accomplished by either thermal or catalytic cracking. At temperatures in excess of 1000° F. and at about atmospheric pressure, propane/butane is catalytically converted to olefins by a variety of processes, such as UOP Oleflex and Houdry Catofin. However, conversion is only about 35–40% per pass, with selectivities in the order of 80%. Thus, only about one-thlird (⅓) of the paraffins, namely propane/butane, fed to a dehydrogenation zone undergo the desired conversion to propylene/butylene. Most of the propane/butane is unconverted, and a small amount is converted to light hydrocarbon gases. The Mobile olefin-to-gasoline and distillate process is particularly well suited to converting the olefins to useful products, gasoline and distillate, which are easy to separate from the unconverted paraffins thus facilitating recycle of paraffins to dehydrogenation. In the Mobil olefin-to-gasoline and distillate process (MOGD) light olefins are converted to gasoline and distillate range hydrocarbons over ZSM-5 catalysts at pressures from 400–1000 psig and temperatures from 300°–600° F. The distillate-to-gasoline ratio depends on the extent of gasoline recycle, light olefin partial pressure and reaction temperature.

The Mobil olefin-to-gasoline and distillate process (MOGD) can advantageously be integrated with catalytic or thermal dehydrogenation processes which convert LPG (propane/butane) into corresponding light olefins (propylene/butylene). The level of integration and extent of advantage depend on the type of dehydrogenation process employed. The extent of integration is likely to be smaller for dehydrogenation processes which use hydrogen recycle (for example, the UOP Oleflex process) and considerably more extensive for processes which do not use hydrogen recycle (for example, the Houdry Catofin process).

The operating conditions for catalytic dehydrogenation depend upon which of the commercially available processes is used. Typical catalytic dehydrogenation conditions range from about 0.1–2 atmospheres and 1000°–1700°. Thermal dehydrogenation operates at similar conditions, however it is less selective for dehydrogenation of propane/butane than catalytic dehydrogenation, so it produces more ethylene. U.S. Pat. No. 4,413,153 (Garwood et al) describes dehydrogenation in more detail.

The invention will now be described in greater detail in connection with specific embodiments thereof illustrated in FIGS. 1–4. These embodiments, however, are not to be construed as a limitation on the scope of the invention, but are merely provided by way of exemplary illustration.

Figure 1:
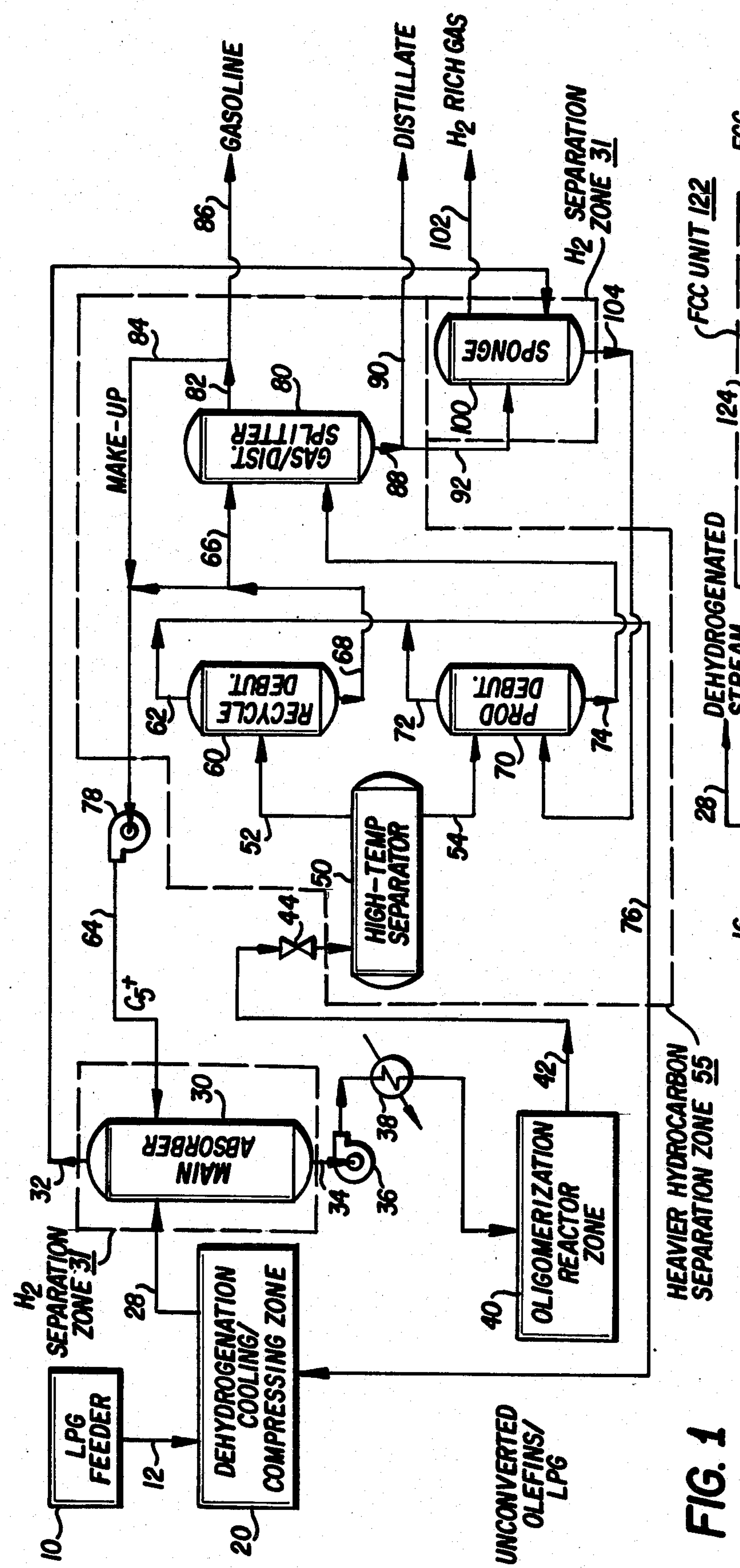
FIG. 1 is a schematic representation showing the process equipment and flow configuration for a preferred embodiment.

Referring to FIG. 1, the preferred apparatus for the method is provided with a means for feeding LPG (liquified petroleum gas) 10 through an LPG feedstream 12 to a dehydrogenation zone 20, which comprises means for dehydrogenating, cooling and compressing the LPG feedstream 12. In the dehydrogenation zone 20, the LPG feedstream is converted to a dehydrogenation effluent stream 28 comprising $C_4^-$ olefins. The conditions in the dehydrogenation zone 20 are set by catalyst technology to give as high a conversion as possible with good selectivity. Within the dehydrogenation zone 20, the olefin rich products are cooled and compressed to about 300 psia before being sent, as dehydrogenation effluent stream 28, to a $H_2$ separation zone 31. The $H_2$ separation zone 31 comprises a main absorber 30, in which the $C_3$–$C_4$ range hydrocarbons from stream 28 are absorbed into a lean oil stream 64, which preferably comprises $C_5^+$ olefins, to separate the $C_3$–$C_4$ range hydrocarbons from the hydrogen and light gases, comprising $C_1$–$C_2$, produced in the dehydrogenation zone 20. An effluent comprising the hydrogen, $C_2^-$, and nominal amounts of $C_3^+$, including some lean oil, exits the main absorber 30 as the $C_2^-$ rich stream 32. The $C_2^-$ rich stream 32 may then be sent to a sponge absorber 100 to separate $H_2$ and $C_4^-$ from $C_5^+$ by contacting stream 32 with a sponge distillate stream 92. Stream 92 absorbs $C_5^+$ material to form a sponge bottom stream 104, while the $H_2$ and $C_4^-$ gases pass from the sponge absorber 100 in a $H_2$ rich gas stream 102.

The $C_3$–$C_4$ and $C_5^+$ materials leave the main absorber through the $C_3^+$ rich stream 34 which is suitable as a feedstock for an oligomerization reactor zone 40. The $C_3^+$ rich stream 34 contains at least one volume, preferably at least 2 volumes, of $C_5^+$ material per volume of $C_3$–$C_4$ olefins (to promote absorption of $C_3$–$C_4$ olefins into the $C_5^+$ material), along with almost all of the propanes and butanes which were unconverted in the dehydrogenation zone 20. An olefin feed pump 36 is provided to pressurize the $C_3^+$ rich stream to about 400–1000 psig, preferably 700–900 psig, and a heater 38 is provided for heating the $C_3^+$ rich stream 34 to a temperature of 300°–600° F. prior to the oligomerization reactor.

In the oligomerization reactor zone 40, about 85–98% of the $C_3$–$C_4$ olefins are converted to gasoline and distillate, thereby facilitating the downstream separation of butane and propane for recycling to the dehydrogenation zone 20. In addition, a portion of the olefins in the recycled lean oil stream 64 oligomerize to distillates. The oligomerization reactor means 40 contains a crystalline zeolite catalyst maintained at a pressure of about 400–1000psig, preferably 700–900 psig, a temperature of about 300°–600° F., with start-of-cycle temperatures around 450° F., and a space velocity of about 0.1–10 weight hourly space velocity (WHSV) with regard to $C_3$ and higher olefins. The distillate-to-gasoline ratio depends on the extent of gasoline recycle, light olefin partial pressure and reaction temperature. It is possible to obtain very high distillate to gasoline ratios (approximately 5:1 volume basis) with high conversion by oligomerization of the $C_3$ and $C_4$ olefins (approximately 95%) if the gasoline recycle ($C_5^+$ material from stream 64) to $C_3$–$C_4$ olefin feed (primarily from effluent stream 28) ratio is at least 1:1 on a volume basis, preferably 2:1, to achieve high adsorption of $C_3$–$C_4$ olefins from the dehydrogenation effluent stream 28, and the $C_3$–$C_4$ olefin partial pressure is at least 160 psia. Preferably, the oligomerization reactor zone 40 comprises a fixed bed downflow pressurized reactor having a porous bed of crystalline zeolite catalyst, such as ZSM-5.

A pressure reduction valve 44 is provided to drop the pressure of reactor effluent stream 42 to about 120–200 psig, after which the depressurized stream 42 is fed to a heavier hydrocarbon separation zone 55. In zone 55, a high temperature separator 50, which operates at lower pressure than the oligomerization zone 40, separates the depressurized stream 42 into a separator vapor stream 52 and separator liquid stream 54. The distillate and gasoline produced in the oligomerization reactor 40, and portion of $C_4^-$, leave the high temperature separator 50 in the separator liquid stream 54, while the majority of the gasoline, which recycles as lean oil, as well as most of the $C_4^-$ leave in the separator vapor stream 52.

Separation zone 55 further comprises dual debutanizers 60,70. The dual debutanizers include a recycle debutanizer 60, which separates the separator vapor stream 52 into a recycle debutanizer overhead stream 62 and a recycle debutanizer bottoms stream 68; and a product debutanizer 70, which separates the separator liquid stream 54 into a product debutanizer overhead stream 72 and product debutanizer bottom stream 74. The recycled debutanizer overhead stream 62 and product debutanizer overhead stream 72 are combined and recycled to the dehydrogenation zone 20 as an unconverted LPG stream 76, which preferably may also comprise less than 5% $C_3$–$C_4$ olefins. A gas/distillate splitter 80 is provided to separate the product debutanizer bottom stream 74 and an optional portion 66 of the recycle debutanizer bottoms stream 68 into a splitter gasoline rich stream 82 and a splitter distillate rich stream 88. The splitter gasoline rich stream 82 may be divided into a gasoline product stream 86, and optionally a $C_5^+$ makeup stream 84. $C_5^+$ makeup stream 84 can be blended with the recycle debutanizer bottoms stream 68, passed through pump 78 and sent to the main absorber 30 as lean oil stream 64. The splitter distillate rich stream 88 may be divided into a distillate product stream 90 and a sponge feedstream 92. A sponge absorber 100 is provided to separate the $C_5^+$ from the hydrogen and $C_4^-$ by contacting the sponge distillate stream 92 with the $C_2^-$ rich stream 32. The sponge absorber 100 absorbs a major portion of the $C_5^+$ carried over from the main absorber 30 to produce a hydrogen rich gas 102 and a sponge bottom stream 104, which passes to the product debutanizer 70.

The benefits of the separation zone 55 include increased energy efficiency for separation of the effluent stream 42 from the catalytic oligomerization zone 40. Some recycle gasoline is absorbed into the distillates in the separator liquid stream 54 and the inefficiency of the gasoline recycle operation is related to the extent that more gasoline is absorbed into stream 54 than is made by oligomerization. Because of overabsorption, it may be necessary to distill stream 74 in the gasoline/distillate splitter 80 to produce $C_5^+$ makeup stream 84, whereas it would be more efficient to recover all the $C_5^+$ required for recycled lean oil stream 64 as a liquid from the recycle debutanizer 60. In the invention, only about 10% of the lean oil stream 64 is distilled overhead in the gasoline/distillate splitter 80. The quantity of the lean oil stream 64 fed to the main absorber 30 is preferably set for high recovery of propylene from the dehydrogenation effluent stream 28, namely, a volume ratio for $C_5^+$ material to $C_3$–$C_4$ olefins of at least 2:1; this amount is about twice what is required for the oligomerization reactor 40.

Conventional dehydrogenation processes have a disadvantage because the thermodynamics of the dehydrogenation reaction of paraffins to olefins is unfavorable. The conversion of LPG range paraffins to olefins is very endothermic. Therefore, supplying the heat for the process leads to a significant part of the large process costs for current technology.

Figure 2:
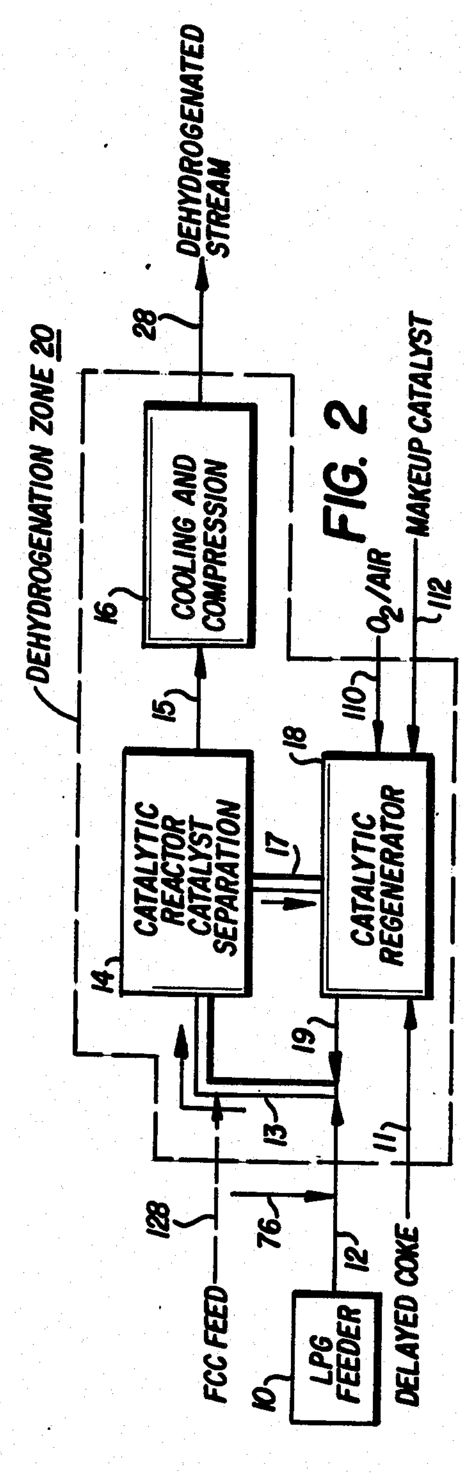
FIG. 2 is a schematic representation of a catalytic reactor and catalytic regeneration system for dehydrogenation of paraffins and an alternate embodiment which also allows fluid catalytic cracking (FCC) of residuum.

FIG. 2 shows an apparatus for a method of dehydrogenation which could be used as the dehydrogenation zone 20 of FIG. 1. The dehydrogenation zone 20 can be modified to use a transport-type reaction system employing fluidizable-type catalysts which improve the dehydrogenation step. Appropriate catalysts would include Group VIII and/or VB metal-contaminated crystalline zeolite FCC catalysts, particularly wherein the contaminating metal includes nickel or vanadium. Typically, the catalysts are contaminated by metal impurities in hydrocarbon streams fed to FCC units in conventional refineries (not shown).

The dehydrogenation zone 20 (FIG. 2) comprises a means for feeding LPG 10, a catalytic reactor/catalyst separation zone 14, a catalytic regenerator 18, and a dehydrogenation riser 13. LPG feedstream 12,76 pass through the dehydrogenation riser 13 in combination with crystalline zeolite catalyst stream 19 from the catalytic regenerator 18, to catalytic reactor 14. Makeup catalyst for the dehydrogenation zone 20 is provided by makeup catalyst stream 112. The catalyst and LPG stream are separated within the catalytic reactor/catalyst separation zone 14, by conventional means such as cyclones, to form a spent catalyst stream, and the dehydrogenation product which exits as catalytic reactor effluent stream 15. Stream 15 passes to a cooling and compression zone 16 to form the dehydrogenation effluent stream 28. A spent catalyst transfer line 17 is provided to pass the spent catalyst stream from the catalytic reactor/catalyst separation zone 14 to the catalytic regenerator 18. The catalytic regenerator 18 combusts coke, formed in the riser 13, along with the hydrocarbons entrained with the spent catalyst with $O_2$ from an $O_2$/air stream 110 to produce catalyst stream 19, which mixes with LPG streams 12,76. Because of the large endothermic heat of reaction and high temperature reactor conditions, a supplemental fuel, such as fluid coke or ground-up delayed coke, may be added to the regenerator 18 through fluid/delayed coke stream 11 to heat balance the operation. Because of the high metals content of the coke, it, in addition to supplying fuel for the process, may assist as a catalyst in dehydrogenation reactions. The dehydrogenation riser 13 would run at temperatures similar to conventional catalytic dehydrogenation (Catofin) ranging from 1000°-1700° F. and pressures from 2-20 psig.

Figure 3:
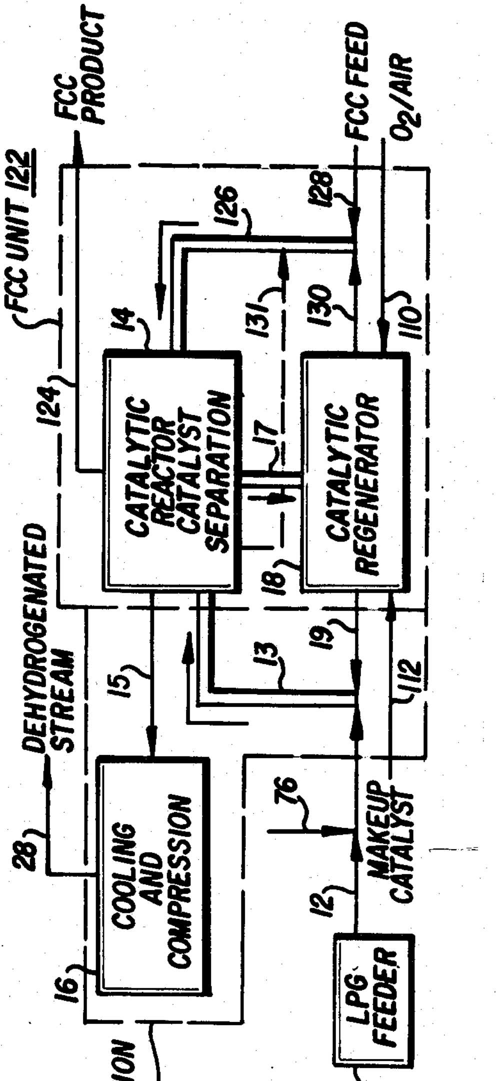
FIG. 3 is a schematic representation of an FCC unit combined with a catalytic dehydrogenation zone.

An alternative embodiment of a dehydrogenation zone 20 is shown in FIG. 3. It employs a metal-contaminated FCC catalyst as part of a residuum cracking FCC unit 122. Appropriate catalysts would include Group VIII and/or Group VB metal-contaminated crystalline zeolite FCC catalysts, particularly wherein the contaminating metal includes nickel or vanadium. Residuum is heavy 650° F.+ b.p. range hydrocarbon material. Such an FCC unit 122 makes coke in excess of that required as fuel, so catalyst cooling is employed to heat balance the FCC unit 122. To better utilize this heat, a dehydrogenation riser 13 is provided in which hot regenerated metal-contaminated FCC catalyst is first contacted with LPG range hydrocarbons from the LPG feedstream 12 and unconverted LPG stream 76 to convert a portion of the LPG to olefins. The amount of LPG is set to heat balance the FCC unit 122 without external catalyst cooling. In the FCC unit 122, catalyst passes as FCC catalyst stream 130 to combine with FCC feedstream 128 comprising hydrocarbon and pass through FCC riser 126 to the catalytic reactor catalyst separation zone 14, where the catalyst and cracked FCC hydrocarbons separate to form an FCC product stream 124, and a spent catalyst stream which passes through spent catalyst transfer line 17 to the catalytic regenerator 18.

A single riser of a multiple riser FCC unit 122 may be utilized for dehydrogenation in the system. The combined dehydrogenation zone 20 and FCC unit 122 apparatus is provided with a dehydrogenation riser 13, which feeds the combined LPG and catalyst stream to the catalytic reactor/catalyst separation zone 14, where catalyst is separated from the dehydrogenation product so that catalyst exits through spent catalyst transfer line 17, while the dehydrogenation product exits through catalytic reactor effluent stream 15 and passes to a cooling and compression zone 16 to form dehydrogenation effluent stream 28. The FCC unit 122 would comprise the catalytic reactor 14 and an FCC riser 126. FCC feed from stream 128 and regenerated catalyst from stream 130 are combined and travel through the FCC riser 126 into the catalytic reactor 14. The spent catalyst exits the catalytic reactor 14 through spent catalyst transfer line 17 and is returned to the catalytic regenerator 18. Makeup catalyst is provided to the catalytic regenerator through makeup catalyst stream 112. If desired, the residence time in dehydrogenation riser 13 may differ from that in FCC riser 126 in order to provide the appropriate residence time for their respective reactions.

As an alternative of this embodiment of dual risers, the hot regenerated catalyst flows in series through the two risers, first through the dehydrogenation riser 13 to the catalytic reactor 14, then through stream 131 and then through riser 126, as shown in FIG. 3. Hot regenerated catalyst may pass through stream 130 to heat balance riser 126, if necessary.

The embodiment of FIG. 2 may be modified to feed LPG stream 12,76 at the upstream end of the riser 13 and feed residuum in FCC feedstream 128 at a location downstream of where LPG streams 12,76 are injected. Thus, riser 13 may dehydrate the LPG paraffins and crack residuum.

A system related to the embodiment of FIG. 3 is disclosed in U.S. Pat. No. 4,032,432 to Owen, which combines the operation of a fluid catalytic cracking (FCC) unit with a catalytic oligomerization zone to provide heat to the catalytic oligomerization zone using excess heat from an FCC unit. A major difference between the present system and the system of the Owen '432 patent is that the dehydrogenation riser 13 runs hotter (1000°-1700° F.), as compared to the oligomerization riser of '432 to Owen (500°-900° F.), and the present system is aided by Group VIII and VB metals contaminated catalysts, wherein the metal contaminant is preferably nickel or vanadium.

Figure 4:
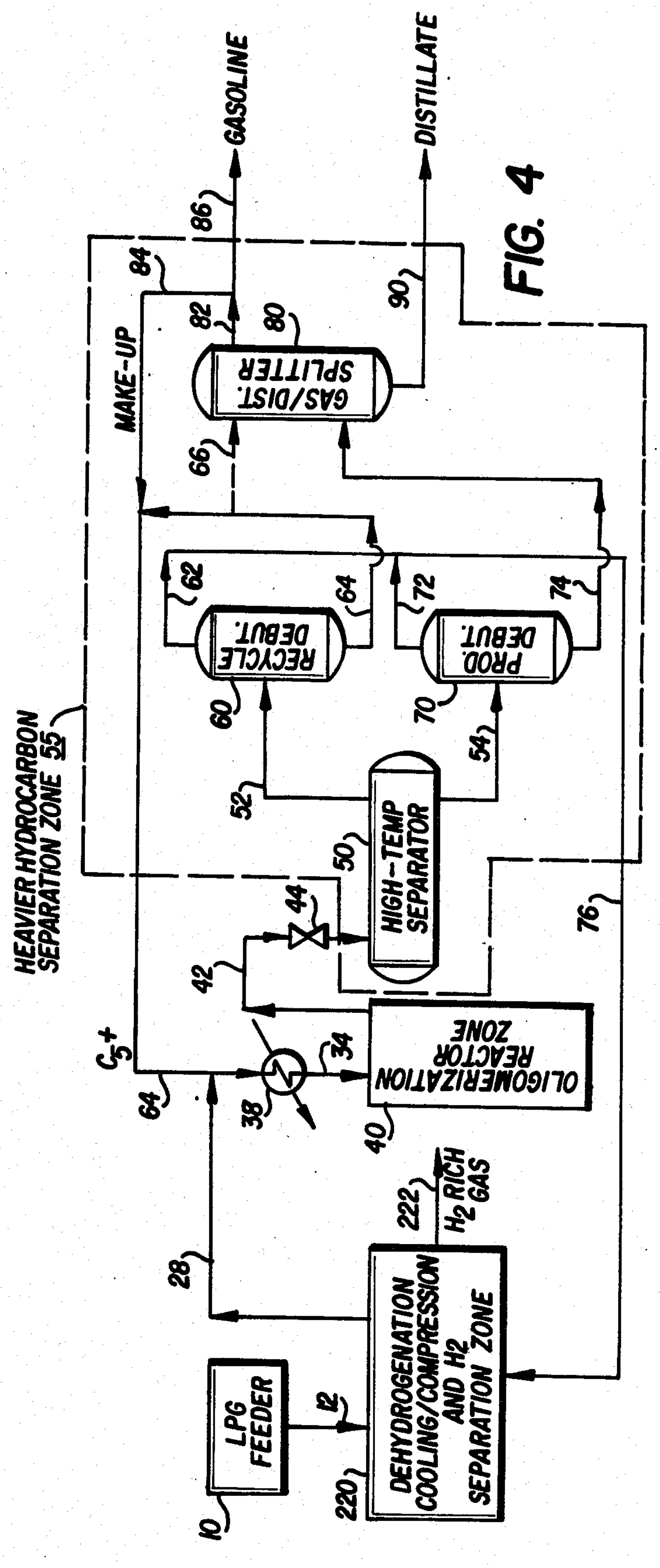
FIG. 4 is a schematic representation showing process equipment and flow configuration for an alternate embodiment.

FIG. 4 illustrates an alternate embodiment of the invention, which comprises the heavier hydrocarbon separation zone 55, a catalytic oligomerization zone 40, and a dehydrogenation zone 220. However, the dehydrogenation zone 220 comprises a means for separating hydrogen in addition to the means for dehydrogenating, cooling and compressing, as discussed above with reference to the dehydrogenation zone 20 of FIG. 1. A suitable process or apparatus which could be included in zone 220 is the UOP Oleflex process discussed above. A cryogenic separating means could be used with the UOP Oleflex process for separating hydrogen in zone 220 to recover an $H_2$ rich gas 222. The UOP Oleflex process includes a hydrogen recycle stream (not shown). The hydrogen recycle stream results in a large circulation of hydrogen within the zone 220, in which case cryogenic separation is more economic than lean oil absorption.

The flow sheet for the embodiment, as shown in FIG. 4, is similar to that of FIG. 1. The principal differences in the embodiments are that the $H_2$ separation zone 31 of FIG. 1, comprising the main absorber 30 and the sponge absorber 100 separation zone, is omitted and the quantity of the lean oil stream 64 is at least 1:1, preferably about 1:1, volume ratio of $C_5^+$ to the $C_3$–$C_4$ olefins in the dehydrogenation effluent stream 28. In order to minimize the amount of gasoline recycle through $C_5^+$ makeup stream 84, the high temperature separator 50, dual-debutanizer 60,70 arrangement is used. Minimizing the amount of gasoline recycle makeup stream 84 is desirable because it reduces the amount of gasoline having to be distilled overhead in the gasoline-distillate splitter 80.

The advantage of the apparatus of FIG. 4 over that of FIG. 1 is that the apparatus of FIG. 4 is suitable when the dehydrogenation zone 20 requires a large hydrogen recycle. A commercially available apparatus, such as UOP Oleflex, employs cryogenic $H_2$ separation to separate $H_2$ from a $C_3^+$ stream within zone 20 containing produced olefins and unconverted paraffins. Thus, the main absorber 30 and associated sponge absorber 100 are eliminated. However, the apparatus of FIGS. 2 and 3 are preferably used in conjunction with the apparatus of FIG. 1.

Process conditions, catalysts and equipment suitable for use in the catalytic oligomerization reactor zone 40 (MOGD) are described in U.S. Pat. No. 3,960,978 (Givens et al); 4,021,502 (Plank et al); 4,413,153; 4,227,992 (Garwood et al); and 4,456,781 (Marsh et al).

The oligomerization catalysts preferred for use in MOGD include the crystalline aluminosilicate zeolites having a silica-to-alumina ratio of at least 12, a Constraint Index of about 1 to 12, and acid cracking activity of about 160–200. Representative of useful ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35; and U.S. Pat. No. 4,046,859 for ZSM-38. The disclosures of these patents are incorporated herein by reference.

A suitable shape selective medium pore catalyst for a MOGD reactor 40 is a HZSM-5 zeolite with alumina binder in the form of cylindrical extrudates of about 1–5 mm. Other catalysts which may be used in a MOGD reactor include a variety of medium pore (approximately 5–9 angstroms) siliceous materials, such as borosilicates, ferrosilicates, and/or aluminosilicates, disclosed in U.S. Pat. Nos. 4,414,143 and 4,417,088, incorporated herein by reference.

While specific embodiments of the method and apparatus aspects of the invention have been shown and described, it should be apparent that many modifications can be made thereto without departing from the spirit and scope of the invention. Accordingly, the invention is not limited by the foregoing description, but is only limited by the scope of the claims appended thereto.

We claim:

1. A process for converting lower paraffinic hydrocarbon feedstock comprising propane and/or butane into heavier hydrocarbons comprising gasoline and distillate, comprising the steps of:

feeding the paraffinic feedstock to a dehydrogenation zone under conversion conditions for dehydrogenating at least a portion of said feedstock;

recovering a first dehydrogenation gaseous effluent stream comprising propene and/or butene;

contacting said first gaseous effluent steam with a liquid lean oil sorbent stream comprising $C_5^+$ hydrocarbons under sorption conditions to produce a $C_3^+$ rich liquid absorber stream and a light gas stream;

sequentially pressurizing, heating and passing said $C_3^+$ rich liquid absorber stream to an oligomerization reactor zone at elevated temperature and pressure;

contacting said $C_3^+$ rich stream with oligomerization catalyst in said oligomerization reactor zone for conversion of at least a portion of lower olefins to heavier hydrocarbons under oligomerization reaction conditions to provide a second reactor effluent stream comprising gasoline and distillate boiling range hydrocarbons;

flash separating said second reactor effluent stream into a separator vapor stream comprising a major portion of said hydrocarbons which later form said lean oil stream, and a major portion of the $C_4^-$ hydrocarbons and a separator liquid stream comprising said gasoline and distillate boiling range materials produced in said oligomerization reactor zone;

fractionating said separator liquid stream in a first product debutanizer tower into a first debutanizer overhead vapor stream comprising $C_4^-$ hydrocarbons and a product debutanizer liquid bottoms stream comprising $C_5^+$ gasoline and distillate boiling range hydrocarbons;

further fractionating said product debutanizer liquid stream in a product splitter tower to provide a gasoline product stream and a distillate product stream;

fractionating said separator vapor stream in a second recycle debutanizer tower into a second debutanizer overhead vapor stream comprising $C_4^-$ hydrocarbons and a $C_5^+$ liquid recycle stream comprising;

recycling said first and second debutanizer overhead vapor streams to said dehydrogenation reactor zone for further conversion; and passing at least a portion of the liquid recycle stream from the second debutanizer tower for use as said liquid lean oil sorbent stream; thereby minimizing lean oil to said product debutanizer and said product splitter downstream.

* * * * *